US009066531B2

(12) United States Patent
Williams

(10) Patent No.: US 9,066,531 B2
(45) Date of Patent: Jun. 30, 2015

(54) PROTEIN RECOVERY

(71) Applicant: AB AGRI LIMITED, London (GB)

(72) Inventor: Peter Edmond Vaughan Williams, Brixworth (GB)

(73) Assignee: AB AGRI LIMITED, London (GB)

( * ) Notice: Subject to any disclaimer, the term of this patent is extended or adjusted under 35 U.S.C. 154(b) by 0 days.

(21) Appl. No.: 14/511,433

(22) Filed: Oct. 10, 2014

(65) Prior Publication Data

US 2015/0024451 A1    Jan. 22, 2015

Related U.S. Application Data

(63) Continuation of application No. 13/257,895, filed as application No. PCT/GB2010/000577 on Mar. 25, 2010, now abandoned.

(30) Foreign Application Priority Data

Mar. 26, 2009 (GB) .................................. 0905234.1

(51) Int. Cl.

| | | |
|---|---|---|
| C12P 7/10 | (2006.01) | |
| A23K 1/00 | (2006.01) | |
| A23K 1/18 | (2006.01) | |
| C12F 3/06 | (2006.01) | |
| C12N 1/02 | (2006.01) | |
| C12N 1/18 | (2006.01) | |
| C12P 7/06 | (2006.01) | |
| A23K 1/16 | (2006.01) | |
| C07C 29/86 | (2006.01) | |

(52) U.S. Cl.
CPC ................. *A23K 1/007* (2013.01); *A23K 1/008* (2013.01); *A23K 1/009* (2013.01); *A23K 1/1813* (2013.01); *A23K 1/1826* (2013.01); *A23K 1/188* (2013.01); *C12F 3/06* (2013.01); *C12N 1/02* (2013.01); *C12N 1/18* (2013.01); *C12P 7/06* (2013.01); *Y02E 50/17* (2013.01); *A23K 1/1631* (2013.01); *C07C 29/86* (2013.01); *C12P 7/10* (2013.01)

(58) Field of Classification Search
None
See application file for complete search history.

(56) References Cited

U.S. PATENT DOCUMENTS

| | | |
|---|---|---|
| 4,055,667 A | 10/1977 | Linton et al. |
| 4,287,303 A | 9/1981 | Dahlberg et al. |
| 4,361,651 A | 11/1982 | Keim |
| 4,447,534 A | 5/1984 | Moebus et al. |
| 4,889,805 A | 12/1989 | Da Silva Telles et al. |
| 5,066,498 A | 11/1991 | McCauley, III |
| 5,364,335 A | 11/1994 | Franzen et al. |
| 2006/0194296 A1 | 8/2006 | Hammond et al. |
| 2008/0095890 A1 | 4/2008 | Watson |
| 2012/0121565 A1 | 5/2012 | Williams |

FOREIGN PATENT DOCUMENTS

| | | |
|---|---|---|
| EP | 0395556 A1 | 10/1990 |
| EP | 0636692 A1 | 2/1995 |
| EP | 1988169 A1 | 11/2008 |
| GB | 2054645 A | 2/1981 |
| WO | 8603514 A1 | 6/1986 |
| WO | 8606098 A1 | 10/1986 |
| WO | 2007038833 A1 | 4/2007 |
| WO | 2010109203 A1 | 9/2010 |

OTHER PUBLICATIONS

Belyea, R. L., et al., "Composition of corn and distillers dried grains with solubles from dry grind ethanol processing," Bioresource Technology, 2004, pp. 293-298, vol. 94, Elsevier Ltd.
Foreign communication from a related application—Examination Report, European Application No. 10711248.4, Sep. 18, 2012, 9 pages.
Foreign communication from a related application—Search Report, United Kingdom Application No. GB0905234.1 Jul. 22, 2009, 2 pages.
Foreign communication from the priority application—International Preliminary Report on Patentability, PCT/GB2010/000577, 9 pages, Sep. 27, 2011.
Foreign communication from the priority application—International Search Report and Written Opinion, PCT/GB2010/000577, 10 pages, Aug. 4, 2010.
Kim, Youngmi, et al., "Composition of corn dry-grind ethanol by-products: DDGS, wet cake, and thin stillage," Bioresource Technology, 2008, pp. 5165-5176, vol. 99, Elsevier Ltd.
Knott, J., et al., "Effects of feeding diets containing spray dried corn condensed distiller's solubles (CDS) and associated fractions on growth performance of early-weaned pigs," J. Anim. Sci., Ref. No. 164, 2005, p. 71, vol. 83, Suppl. 2, ASAS/ADSA Midwest Mtg. Abstract.
McDonald, Peter, et al., "Animal Nutrition," Oct. 1981, 3rd edition, ISBN: 0582443997, Prentice Hall Press.
Neutkens, Debra, "Ethanol Byproduct May Be Diet Alternative," National Hog Farmer, Feb. 15, 2005, 3 pages, http://www.nationalhogfarmer.com/mag/farming_ethanol_byproduct_may/index.html, Penton Media, Inc.

(Continued)

*Primary Examiner* — Kade Ariani
(74) *Attorney, Agent, or Firm* — Conley Rose, P.C.; Rodney B. Carroll

(57) ABSTRACT

A process for recovering a protein-containing fermentation agent, comprising (i) forming an aqueous mixture of an organic material and a protein-containing fermentation agent capable of fermenting the organic material to produce ethanol, (ii) fermenting the aqueous mixture to produce ethanol, (iii) recovering from the fermented aqueous mixture an ethanol stream which is rich in ethanol and a co-product stream comprising unfermented organic material, fermentation agent and an aqueous solution of dissolved solids in water, (iv) subjecting the co-product stream to a first separation stage to recover a first stream rich in the unfermented organic material and a second stream rich in the fermentation agent suspended in the aqueous solution, and (v) subjecting the second stream to a second separation step, capable of recovering suspended solids from a liquid, to recover a third stream rich in the fermentation agent and a fourth stream rich in the aqueous solution. The invention also relates to a new yeast composition obtainable from the process.

30 Claims, 3 Drawing Sheets

(56) References Cited

OTHER PUBLICATIONS

Office Action dated Nov. 1, 2013 (61 pages), U.S. Appl. No. 13/257,895, filed on Jan. 6, 2012.

Office Action dated Apr. 11, 2014 (22 pages), U.S. Appl. No. 13/257,895, filed on Jan. 6, 2012.

Rausch, Kent D., et al. "The Future of Coproducts from Corn Processing," Applied Biochemistry and Biotechnology, 2006, pp. 47-86, vol. 128, Humana Press Inc.

1 page abstract cited in Nov. 1, 2013 Office Action for related U.S. Appl. No. 13/257,895 plus 1 page additional abstract. [Wang, H., et al., "Effect of the Corn Breaking Method on Oil Distribution between Stillage Phases of Dry-Grind Corn Ethanol Production," J. Agric. Food Chem., 2008, pp. 9975-9980, vol. 56, No. 21, American Chemical Society.].

PROTEIN RECOVERY

CROSS-REFERENCE TO RELATED APPLICATIONS

This application is a continuation of and claims priority to U.S. patent application Ser. No. 13/257,895 filed Jan. 6, 2012 entitled "Protein Recovery" which is a filing under 35 U.S.C. 371 of International Application No. PCT/GB2010/000577 filed Mar. 25, 2010 entitled "Protein Recovery," claiming priority of Great Britain Patent Application No. 0905234.1 filed Mar. 26, 2009, which applications are incorporated by reference herein in their entirety.

FIELD OF INVENTION

The present invention relates to recovery of protein-containing material, and more particularly relates to a process for recovering a protein-containing material, such as yeast, from a bio ethanol process. The invention also relates to a new protein-containing composition, which may be obtained as a co-product of a bio ethanol process. The protein-containing composition according to the invention is particularly useful in animal feed material.

BACKGROUND OF INVENTION

It has been known for many years to use bio ethanol refineries to convert biological material into useful chemical products. In a typical bio refinery, a plant material, such as grain containing starch (e.g., wheat or maize), is treated to produce ethanol (so-called "bio ethanol"). The process can be used to produce both potable alcohol and industrial ethanol.

For example, in a conventional bio ethanol plant, wheat is fermented using yeast as the fermentation organism to produce bio ethanol as a main product and by-products, such as animal feed. The ratio of bio ethanol to by-products is approximately 1:1, on a weight basis.

The principle by-product of a bio ethanol plant is called distillers dark grains and solubles ("DDGS"). DDGS is used in the animal feed market, primarily as a feedstock for ruminants. In a conventional process, after the ethanol has been produced by fermentation, it is separated from the fermentation products by distillation.

The residue after distillation of the ethanol (termed whole stillage) is then dried to produce the by-product, DDGS. To aid in drying, the whole stillage is separated into two fractions, a solids fraction and a liquid fraction. This first separation may be carried out in a decanter to produce a solid and a liquid output. The solid output may be pressed into a cake. The liquid output is subjected to evaporation to make a syrup containing, among other things, yeast—this syrup is known as condensed distiller's solubles (CDS). The CDS is then added to the pressed cake and dried to form what is known as the DDGS.

Although the bio ethanol process has been used for many years, very little work has been done on further development of the by-products of the process, and there is very little published information about by-product development.

In a paper by J. Knott and G. Shurson (Effects of feeding diets containing spray dried corn condensed distiller's solubles (CDS) and associated fractions on growth performance of early-weaned pigs), J. Knott, G. Shurson, M. Hathaway, and L. Johnston, J. Anim Sci. Vol 83 (Suppl.2) p. 71; Ethanol Byproduct may be a diet alternative, National Hog Farmer. Feb. 15, 2005) work was done on the CDS by-product of bio ethanol plants. The authors separated the CDS into two products, yeast cream (YC) and residual solubles (RS). The products were tested for utility as feed additives in animal feed. The purpose of the study was specifically to test whether the by-products of the bio ethanol process had any utility as growth factors.

The Knott/Shurson paper describes subjecting the CDS to a spray drying process to separate the CDS into three fractions, called "sprayed dried distiller's solubles," "spray dried yeast cream," and "spray dried residual solubles." This process would not be suitable for the large scale recovery of yeast, because its cost would be prohibitive. Furthermore, based on the disclosure of the Knott/Shurson paper, there would be no motivation for the skilled person to seek to recover yeast on a large scale, as the paper is concerned with the use of small quantities of yeast as a growth factor present in the mixture, and does not make any reference to the amount of yeast which may be available for recovery from the CDS or the large scale recovery of yeast per se.

SUMMARY OF THE INVENTION

It is known that yeast is a by-product of the bio ethanol process, and indeed this is inevitable, as the process itself relies on the presence of yeast for the fermentation.

Yeast has been used in the animal feed market for many years, when as a dead yeast as feed material and live yeast as a feed additive. Yeast has a high content of digestible protein, and is therefore potentially useful as a feed material for use in animal feed. However, to date, yeast has not been used to any significant extent as a feed material, owing to the lack of availability of sufficient quantities of the material at a cost effective price compared to other feed materials. In commercially available animal feeds, there is a wide range of high protein feed materials of which, rape meal, soya bean meal, and fishmeal are primary examples. There are some examples of dried yeast being used on a commercial basis as a feed material for fish, but it has not been used for animals, such as ruminants (cattle and sheep) or mono-gastrics, such as pigs. Yeast is mostly used as a feed additive in amounts generally less than 2 wt % of the total weight of animal feed when it is used with relevant claims to improve the performance of animals.

It would be desirable to use yeast as a feed material for supplying digestible protein to animals, but except in certain limited circumstances (such as the aquatic use mentioned above), it is not feasible to do so. This is because of the cost of the available yeast is too high.

During the bio ethanol fermentation process, the yeast is added into the mixture after saccharification in order to ferment the carbohydrate substrate. The quantity of yeast added may be large and sufficient to ferment the substrate available or may be added in a smaller quantity and allowed to multiply in the medium to the point at which there is sufficient yeast to ferment the total available carbohydrate.

We have now unexpectedly found that the quantity of yeast produced as a by-product of the bio ethanol production process is much higher than had been appreciated. In particular, we have found that the amount of yeast produced as a by-product is in the range 10-20 wt %, based on the total weight of the by-products. This typically represents about 4-7 wt % of the total output mass from the process, which is much higher than the amount which would be expected.

We have also found that a new yeast containing composition can be recovered from a bio ethanol process, which has an unexpected positive effect on the growth of animals.

BRIEF DESCRIPTION OF THE DRAWINGS

Reference is now made to the accompanying drawings, in which.

DETAILED DESCRIPTION OF THE INVENTION

Figure 1:
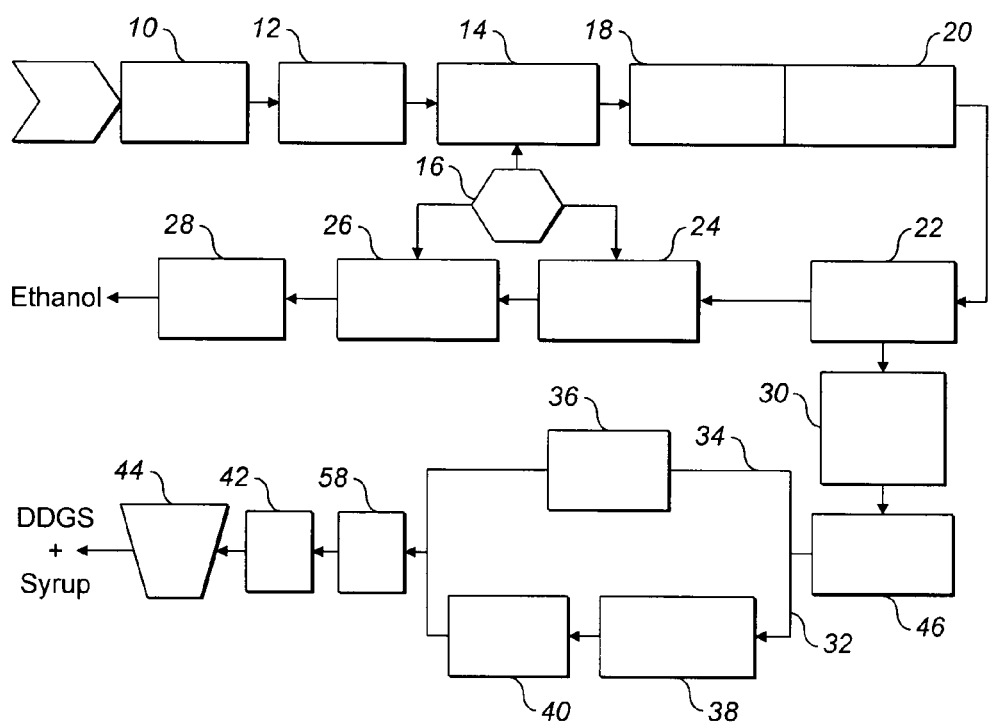
FIG. 1 is a schematic drawing of an embodiment of a bio ethanol process according to the prior art.

Ethanol had been produced from bio ethanol plants on a large scale for the past 15 to 20 years. For example, the European annual capacity for bio ethanol production in 2008 had risen to over 4 billion liters. However, in the prior art, the yeast fraction has never been recovered on a commercial scale either from the process itself or from by-products of the bio ethanol process, because it had not been appreciated that there was a significant amount of it present, or that it could be efficiently recovered. In the prior art, the yeast was not available at a price or quantity such that it could be conveniently used as a feed material in animal feed.

According to one aspect of the invention, there is provided a process for recovering a protein-containing fermentation agent, comprising: forming an aqueous mixture of an organic material and a protein-containing fermentation agent capable of fermenting the organic material to produce ethanol; fermenting the aqueous mixture to produce ethanol; recovering from the fermented aqueous mixture an ethanol stream which is rich in ethanol and a co-product stream comprising unfermented organic material, the fermentation agent and an aqueous solution of dissolved solids in water; subjecting the co-product stream to a first separation stage to recover a first stream rich in the unfermented organic material and a second stream rich in the fermentation agent, which is suspended in the aqueous solution; subjecting the second stream to a second separation step, capable of recovering suspended solids from a liquid, to recover a third stream rich in the fermentation agent and a fourth stream rich in the aqueous solution; and, if necessary, drying the third stream to recover a composition comprising the fermentation agent.

The fermentation agent may be any agent used in the fermentation of organic materials to produce ethanol. In one embodiment, the fermentation agent comprises, and more preferably consists of, fungal cells. More specifically, the fungal cells comprise, and more preferably consist of, single-celled ascomycetous fungal cells, particularly yeast. In the preferred embodiment, the yeast is of the genus *Saccharomyces*. Yeast of the genus *Saccharomyces Carlsbergiensis* is particularly suitable.

In the following description, the process will be described with particular reference to the recovery of yeast, but it will be appreciated that this description is equally applicable to the recovery of protein containing fermentation agents, including microbial protein-containing cells other than yeast. Furthermore, in another embodiment, the fermentation agent may be a bacterial fermentation agent, such as zymomonas mobilis. The process according to the invention is suitable for any process for the fermentation of organic material to form ethanol (which may be ethanol for industrial use, or potable ethanol). In general, by "fermentation" is meant the biological process by which sugars, such as glucose, fructose and sucrose are converted to carbon dioxide and ethanol.

In accordance with conventional processes, the ethanol stream may be separated from the co-product stream by distillation.

It has not previously been appreciated that the yeast is present in the co-product stream as a suspension, and that it may be separated from the co-product stream by any process suitable for removing a solid suspension from a liquid. In an advantageous embodiment, the separation process is a mechanical separation process, in particular centrifugation. One particularly advantageous process for separating the yeast from the other co-products is known as disk stack separation which employs centrifugal force to separate particulate matter from a liquid. The technique of disk stack separation, per se, is known in the art, but it has not previously been applied to the process according to the invention.

The co-product stream is known in the art as "whole stillage." It comprises predominantly water, undissolved unfermented organic material and undissolved fermentation agent, such as yeast. It also contains non-starch polysaccharides. For example, when the fermented organic material is wheat, the whole stillage contains NSPs based on arabinose, urinic acid, glucan, xylose, and glucose residues and also contains glucomannan. The NSPs in wheat are approximately 25 wt % water soluble and 75 wt % water insoluble. Of the soluble fraction over 90 wt % of the NSPs are arabinoxylan or beta-glucan, with the remainder being galactose. The water is an aqueous solution containing dissolved solids, including unfermented soluble organic material. According to the invention, the undissolved unfermented organic material, which is typically of a fibrous consistency, is separated from the rest of the whole stillage in a first separation step, leaving the aqueous solution and the fermentation agent. It will be appreciated that the unfermented organic material separated from the rest of the whole stillage will still contain some fermentation agent and some of the aqueous solution. However, the majority of the fermentation agent and the aqueous solution is separated from the undissolved unfermented material in the first stage of the separation. The undissolved unfermented organic material may contain a useful amount of the fermentation agent, such as yeast. Therefore, if desired, part of the recovered undissolved unfermented organic material may be recycled back into the co-product stream to improve the yield of fermentation agent.

It has not previously been recognised that the fermentation agent, in particular the yeast, is suspended in the aqueous solution and can be readily separation by a mechanical separation technique, or equivalent. Thus, the majority of the fermentation agent, in particular the yeast, may be separated from the aqueous solution. However, the recovered fermentation agent, in particular the yeast, does usually include some of the aqueous solution (including dissolved solids such as soluble non-starch polysaccharides), and therefore it is preferably dried after recovery.

In a preferred embodiment, the third stream is subjected to a dewatering step. The dewatering step preferably comprises a mechanical dewatering step. The mechanical dewatering step preferably comprises subjecting the third stream to a filter press. It is preferred that the third stream is further dried, preferably by evaporation, preferably with heating, after the dewatering step.

It is particularly advantageous that the fermentation agent, in particular the yeast, is separated from the stillage prior to subjecting the stillage or fermentation agent to any drying or evaporation step. However, it is possible, to dry the stillage, including the yeast, prior to any separation step, then to wet it again, by adding water, when it is desired to separate the fermentation agent from the stillage. This may be useful, for example, when it is desired to separate the fermentation agent from the stillage at a different location from the bio refinery.

The fibrous co-product (i.e., the separated undissolved unfermented organic material) may be processed into a cake to form Distillers Dried grains (DDG).

According to another aspect of the invention, there is provided apparatus for producing ethanol and a fermentation agent, comprising: a fermentation stage for fermenting an aqueous mixture comprising an organic material and a protein-containing fermentation agent capable of fermenting the organic material, to produce ethanol; a first separation stage for recovering the ethanol from the unfermented aqueous mixture; a second separation stage, downstream of the first separation stage for recovering unfermented organic material from the fermentation agent and an aqueous solution of dissolved solids in water; and a third separation stage, downstream of the second separation stage, for separating the fermentation agent into a third stream rich in the fermentation agent and a fourth stream rich in the aqueous solution. Optionally, a drier is provided for drying the third stream.

The starting material for the process may be any organic material (in particular, a starch-containing material or a cellulose-containing material) capable of being fermented with the fermentation agent to produce ethanol. Thus, the starting material may be a cereal grain, such as maize, wheat, sorghum, or barley, or may be potato or beet. Alternatively, the organic material may be straw, wood, or corn stover. The ethanol output may be of a grade used for industrial or fuel use, or it may be of a grade used for human consumption, such as a variety of whisky.

It will be appreciated that the fermentation agent may, and usually will, alter in nature during the course of the process. In general, the fermentation agent used in the fermentation step is "unspent," whereby it is capable of fermenting the organic material. The fermentation agent in the co-product stream may be a mixture of spent and unspent fermentation agent, and is usually substantially entirely spent fermentation agent.

Thus, when the fermentation agent is yeast, unspent (or "live") yeast will be employed during the fermentation process, and by the end of the process, when recovered in the co-product stream, some or all of the yeast will be spent (or "dead") yeast.

In this specification, the expression "fermentation agent" may refer to unspent or spent fermentation agent, and the expression "yeast" may refer to unspent or spent yeast. The composition will be clear to a person skilled in the art from the context in which the terms are used.

According to another aspect of the invention, there is provided a process for treating stillage, the stillage being obtained from a fermentation process, especially an ethanol fermentation process, and comprising water, yeast, suspended fibrous and non-fibrous solids and dissolved solids, the process comprising: separating the majority of the suspending fibrous solids from the rest of the stillage; and then separating the majority of the yeast from the water and dissolved solids. It will be appreciated that the process according to the aspect of the invention may be provided with any desired combination of the features described above in relation to the first aspect of the invention.

The recovered fermentation agent, especially the yeast (typical examples *Saccharomyces cerevisiae; Saccharomyces Carlsbergiensis*) produced by the process or apparatus according to the invention may be formulated for any desired end use, and may be formulated for use as a micronutrient feed additive. However, it is particularly preferred that the fermentation agent, especially the yeast, produced by the process according to the invention is formulated as a feed material in an animal feed composition. The fermentation agent, especially the yeast, may be as a feed material for ruminant animals, such as cattle, sheep and goats. It is particularly preferred that the feed material containing the fermentation agent, especially the yeast, is formulated to feed monogastric animals, such as pigs, poultry, fish, crustacea and companion animals, such as horses, cats and dogs.

The main components of the organic dry matter of food are defined as carbohydrates, lipids, proteins, nucleic acids, organic acids and vitamins (Animal Nutrition, third edition, P. McDonald, R. A. Edwards and J. F. D. Greenhalgh, ISBN 0-582-44399-7). Typically, the fermentation agent, especially the yeast, would be formulated in an animal feed composition in the range from 2 to 40 wt %, preferably 3 to 40 wt %, more preferably 4 to 40 wt %, still more preferably 5 to 40 wt %, with the remainder comprising those components as defined above. In addition, the food may contain a wide range of additives which according to the definition are feed materials which have some special effect, e.g., provide enhanced performance. The protein in the feed material may be provided partly or entirely by the fermentation agent, especially the yeast, produced by the process or apparatus according to the invention.

Other ingredients, such as selected amino acids (such as lysine, methionine, and so on), and vitamins (such as A, D, E, and so on), minerals (such as calcium, phosphorus, and so on) and antibiotics may also be present in the composition.

The process and apparatus according to the present invention produce a high value protein-containing composition as a co-product, rather than the relatively low value DDGS by-product produced in the prior art. The protein-containing composition can be produced on a scale large enough to enable it to be used as a feed material in animal feed.

As mentioned above, the process and apparatus according to the invention have led to a new composition that has not been described in the art before.

Thus, according to another aspect of the invention, there is provided a protein containing composition obtainable by a process as described above.

Furthermore, according to a still further aspect of the invention, there is provided a protein-containing composition comprising yeast in combination with at least one, and preferably more than one, non-starch polysaccharide (NSP), wherein the yeast comprises at least 60 wt % of the composition, based on the dry weight of the composition. Preferably, the composition comprises at least 65 wt % yeast, based on the dry weight of the composition. More preferably, the composition comprises at least 75 wt % yeast, based on the dry weight of the composition. Still more preferably, the composition comprises at least 90 wt % yeast, based on the dry weight of the composition. Most preferably, the composition comprises at least 90 wt % yeast, based on the dry weight of the composition. In these embodiments, the composition typically contains at most 99.5 wt % yeast, 99 wt % yeast, 98 wt % yeast or 95 wt % yeast, based on the dry weight of the composition. The most preferred compositions have from 60 to 95 wt % yeast, based on the dry weight of the composition, most preferably 90 to 95 wt % yeast, based on the dry weight of the composition.

Preferably, the yeast also includes sucrose; at least one reducing sugar; at least one mineral; at least one water soluble oligosaccharide; or a combination thereof. The reducing sugar may be glucose, fructose, lactose, or a combination thereof. Preferably, the composition contains 0 to 8 wt % reducing sugar, more preferably 2 to 8 wt % reducing sugar, still more preferably 4 to 8 wt % reducing sugar and most preferably about 6 wt % reducing sugar.

Preferably, the composition contains 0 to 10 wt % sucrose, more preferably 4 to 10 wt % sucrose, most preferable about 8 wt % sucrose.

Preferably, the composition contains 0 to 4 wt % mineral, most preferably about 2 wt % mineral. The mineral content may contain calcium, magnesium, phosphorous, potassium, sodium, copper, manganese, zinc, or a combination thereof.

The or each NSP is preferably present in an amount up to 10 wt % of the composition. More preferably the NSP is present from 0.1 to 10 wt %, more preferably from 0.1 to 5 wt % more preferably from 1-3 wt % and most preferably about 2 wt %. Preferably, the NSP comprises arabinoxylan, beta-glucan, galactose, or a combination thereof. In an embodiment, the NSP comprises arabinoxylan and beta-glucan. In another embodiment, the NSP comprises beta-glucan and galactose. In another embodiment, the NSP comprises arabinoxylan and galactose. In another embodiment, the NSP consists of arabinoxylan, beta-glucan, and galactose. In another embodiment, the NSP comprises arabinoxylan, beta-glucan, and galactose. Preferably, the NSP comprises at least 90 wt % arabinoxylam and beta-glucan, and more preferably the balance is galactose.

The water content of the composition is preferably 5 to 10 wt %, typically 8 wt %.

It will be apparent that the protein-containing composition according to the invention may be readily produced by the process and apparatus according to the invention, as discussed above. However, this is a new product, which may also be produced by other means, such as by mixing yeast from another source with a preselected amount of NSPs.

According to another aspect of the invention there is provided a feed material comprising a protein-containing composition as described above. Typically, the feed material comprises 2 to 40 wt %, of the protein-containing composition according to the invention, preferably 3 to 40 wt %, more preferably 4 to 40 wt %, still more preferably 5 to 40 wt %. The remainder of the composition may be made up with other desired components, such as a carbohydrate source, and/or a lipid source, and/or food additives. We have surprisingly found that the compositions produced by the above described process and the composition according to the invention is useful in stimulating growth of animals. In particular, the compositions are useful in the non-therapeutic stimulation of growth in animals.

Thus, according to another aspect of the invention, there is provided a method of stimulating growth in an animal comprising administering a growth stimulating amount of a composition as described above.

The method is particularly useful in stimulating growth in cattle, sheep, goats, pigs, poultry, fish, crustacea, horses, cats, and dogs.

The protein composition according to the invention may be included in dietary formulations for livestock as an alternative source of protein to replace a range of protein materials that are currently used either individually or in a mixture in feed (e.g., fishmeal; soya bean meal; rapeseed meal; maize gluten meal; pea protein). As such, the protein composition could replace from 0.5% to 100% of the individual proteins or mixture of proteins in the diet. Preferably, the protein composition according to the invention may replace about 5 to 40 wt % of the proteins in the proteins in the diet, more preferably about 20 to 35 wt %. Typically, the protein composition according to the invention may replace about 30 wt % of the proteins in the diet—this is especially appropriate for fish.

Over a wide range of species (pigs, poultry, fish) the intake per unit metabolic weight (W0.75) of the protein composition according to the invention may range from 0.01 to 90 g dry matter/W0.75/day.

With reference to FIG. 1, a source of fermentable carbohydrate, more particularly a source of starch, such as wheat or maize, is fed to a milling stage 10, then slurried with water to form a mash in a mashing stage 12. The first step in starch breakdown involves saccharification, typically using $\alpha$-amylase and steam. This is followed by a liquefaction stage 14, using steam from a stage 16. Further, enzymes (e.g., gluco amylase) are added in a saccharification stage 18, and yeast is added in fermentation stage 20.

The fermentation produces ethanol and co-products which are discharged to a distillation stage 22, in which the majority of the ethanol is separated by distillation from the majority of the co-products. One output from the distillation stage 22 is an ethanol rich stream, which is fed to a rectification stage 24, in which the ethanol is further purified. Steam from stage 16 is also fed to the rectification stage 24.

The purified ethanol from the rectification stage 24 is fed to a dehydration stage 26, to which further steam from the stage 16 is added. The output from the dehydration stage 26 is discharged to an ethanol storage stage 28.

The co-products from the distillation stage 22, known as whole stillage, are fed to a spent wash tank stage 30, and subsequently to a decanter 32, which separates the solid unfermented organic material from an aqueous phase comprising mostly water and yeast.

The solids output 34 from the decanter 46 is pressed into a cake in a compression stage 36. The liquid output 32 from the decanter 46 is fed to an evaporation stage 38, which removes some water, followed by a further heating stage 40, which removes more water to produce a syrup. This syrup typically has a moisture content of 75 wt % water. The syrup from stage 40 is sprayed onto the cake in a stage 56, and the resultant sprayed cake is fed to a drying stage 42. The output from the drying stage 42 is DDGS, which is fed to a pelleting stage 44, which may also include a cooling stage.

The process shown in the drawings is known as a "dry-grind" process, and this is the preferred process. An alternative process, known as a "wet-grind" process may be used instead, in which an amount of fibre is separated from the starch source prior to fermentation.

Figure 2:
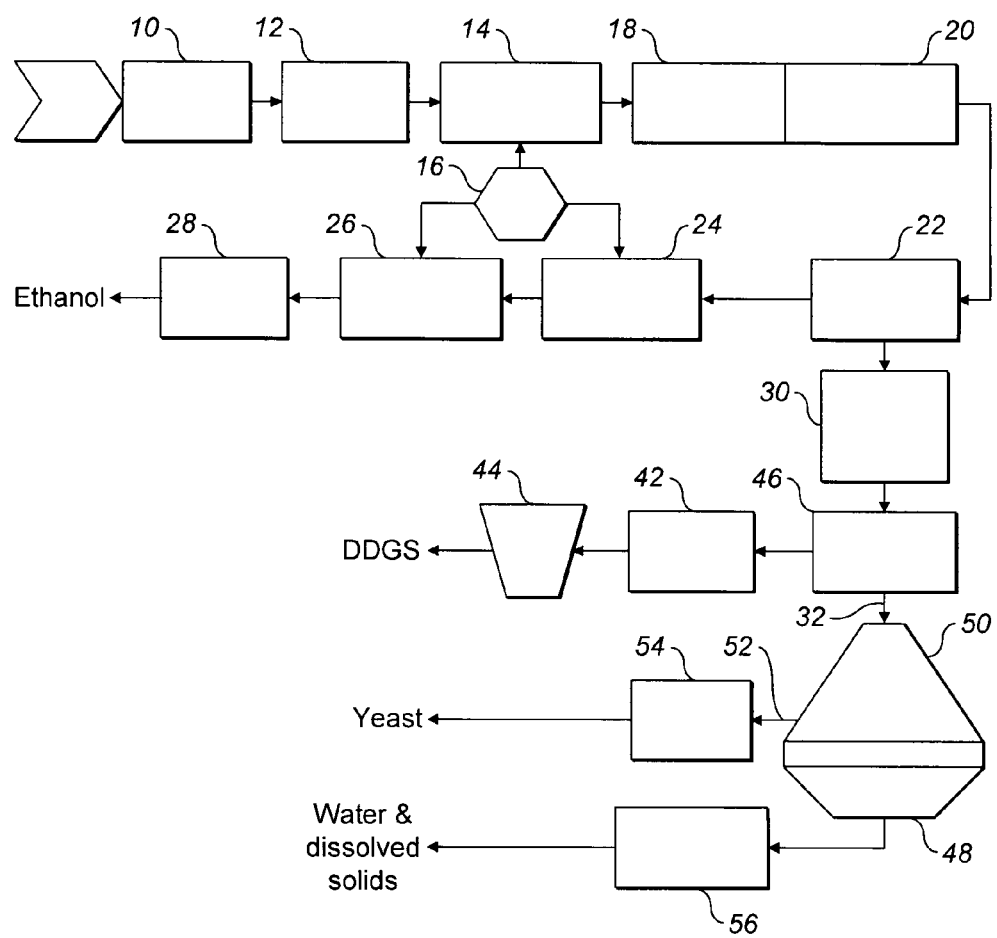
FIG. 2 is a schematic drawing of an embodiment of a process for recovering fermentation agent, in particular yeast, according to the invention.
Figure 3:
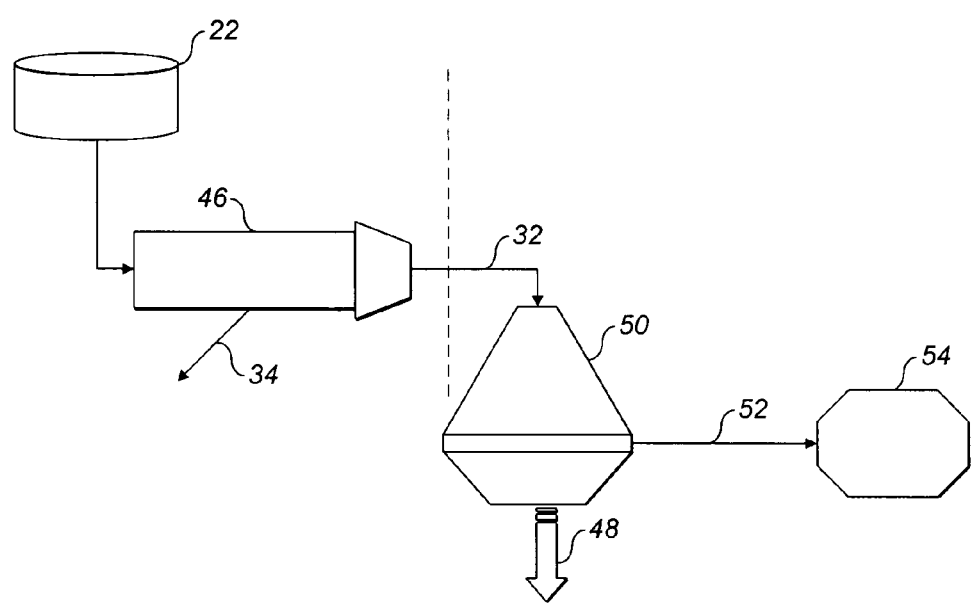
FIG. 3 is a more detailed drawing of part of the process shown in FIG. 1.

Referring now to FIGS. 2 and 3, the process according to the invention is shown. Many of the stages used in the process according to the invention may be identical to the stages shown in FIG. 1, and like parts have been designated with like reference numerals.

The solids output from the decanter 46, is still pressed into a cake in stage 36, then dried and pelletised in stage 42 and 44.

We have found that the liquid output from the decanter comprises a large quantity of yeast suspended in water, and that the yeast can be recovered from the water in a simple mechanical separator. Recovery of yeast at this stage has not been previously contemplated. Thus, the liquid output is fed to a disk stack separator 50 which separates the yeast from the liquid. The yeast is produced in a stream 52, which is fed to a yeast drier 54. The water is produced in a stream 48, which is fed to evaporators 56 to produce a syrup. This syrup may be sprayed onto the DDGS cake, as described with respect to FIG. 1.

EXAMPLES

Reference is now made to the following examples.

Example 1

300 carp fingerlings were fed one of five diets in which the protein containing composition (yeast protein concentrate) was used to replace alternative dietary protein sources over the growth phase of carp from approximately 10 to 50 g live weight. The protein containing composition was used to replace 7.7, 15, 20 and 50% of the dietary protein.

There were three tanks of fish per treatment (20 fish per tank), with each tank representing the experimental unit. Weight gain data was analysed by Analysis of Variance with Tukeys applied post hoc.

Table 1 shows weight gain was increased in all fish given diets containing the protein containing composition compared with the control. Furthermore, this was significant at 14 and 19.7%.

TABLE 1

Yeast tested at 7.5, 15, 20 and 50% of total dietary protein level
Carp trial 1

| Treatments | Initial weight (g) | Final weight (g) | P value (relative to control) |
| --- | --- | --- | --- |
| Control | 12.15 | 39.22 | — |
| 6% unwashed yeast | 12.23 | 41.38 | 0.186 |
| 14% unwashed yeast | 12.27 | 45.92 | <0.001 |
| 19.7% unwashed yeast | 12.42 | 48.00 | <0.001 |
| 46% unwashed yeast | 12.38 | 41.73 | 0.104 |

In the second trial, two forms of the protein containing composition were compared. Two tanks per treatment were used, each containing 25 carp fingerlings. The unwashed form in which the protein containing composition contained the yeast plus the non starch polysaccharides as in trial 1 and a second composition in which the protein containing composition was washed to produce a pure yeast product.

TABLE 2

Comparison of washed and unwashed yeast protein concentrates
Carp trial 2

| Treatments | Initial weight | Final weight | P value (relative to control) |
| --- | --- | --- | --- |
| Control | 15.26 | 55.52 | — |
| 30% Unwashed yeast | 15.20 | 60.00 | 0.947 |
| 30% Washed yeast | 15.14 | 54.40 | 1.000 |

There was a tendency for the fish fed the diet containing the protein containing composition plus the non starch polysaccharides (unwashed yeast) to have weight gains which were higher than both the controls and the fish given the diet containing the washed pure yeast product.

These examples shows that weight gain of fingerling carp was significantly increased when the protein containing composition was used to supply 15-30% of dietary protein for carp. A yeast containing product derived from bio-ethanol production appears to provide a viable alternative protein source for use in commercial diets for fish.

Example 2

140 male Ross 308 chicks were fed one of seven wheat/soya bean meal-based mash diets from 0 to 14 days of age. The diets used contained 0, 3, 6 or 9% of two fermented wheat co-products, one from a potable alcohol source (yeast A) and one from a bio ethanol source (yeast B—i.e., a protein containing composition according to the invention, including NSPs). A control comprising soyabean meal was also used.

Data were analysed using a 2 by 3 factorial design using Genstat version 12 for windows to examine the effects of yeast source and rate of dietary inclusion on viscosity of ileal digesta supernatant, body weight gain, feed intake and feed conversion ratio.

Table 1 shows weight gain was significantly increased in birds fed the bio ethanol-derived yeast source (yeast B), compared to the potable alcohol-derived yeast source (yeast A). Feed intake was also significantly increased in the birds fed diet B but no significantly difference in feed conversion ratio (FCR) was observed between the two yeast sources.

This example shows that yeasts increased broiler weight gain at the lower inclusion levels. Yeast derived from bio-ethanol production appears to provide a viable alternative protein source for use in broiler starter diets.

| Treatment | Mean weight gain (S.E.) (g) | Mean feed intake (S.E.) (g) | FCR |
| --- | --- | --- | --- |
| Control | 240.0 | 380.7 | 1.59 |
| 3% Yeast A | 286.5 | 417.2 | 1.46 |
| 6% Yeast A | 223.5 | 346.8 | 1.55 |
| 9% Yeast A | 202.5 | 326.9 | 1.61 |
| 3% Yeast B | 328.4 | 467.3 | 1.42 |
| 6% Yeast B | 330.4 | 457.0 | 1.38 |
| 9% Yeast B | 265.2 | 427.8 | 1.61 |
| Variation Source | P value | | |
| Yeast source | 0.023 | 0.019 | 0.114 |
| RoI (L) | 0.623 | 0.711 | 0.043 |
| Yeast* RoI | 0.399 | 0.461 | 0.598 |

It will be appreciated that the invention described above may be modified in accordance with the following claims.

The invention claimed is:

1. A process for recovering a protein-containing fermentation agent, comprising:
   (i) forming an aqueous mixture of an organic material and a protein-containing fermentation agent capable of fermenting the organic material to produce ethanol;
   (ii) fermenting the aqueous mixture to produce a fermented aqueous mixture comprising ethanol;
   (iii) recovering from the fermented aqueous mixture an ethanol stream which is rich in ethanol and a co-product stream comprising unfermented organic material, protein-containing fermentation agent and dissolved solids in water;
   (iv) subjecting the co-product stream to a first separation stage to recover a first stream rich in the unfermented organic material and a second stream rich in the protein-containing fermentation agent suspended in water; and
   (v) subjecting the second stream to a second separation stage, capable of recovering suspended solids from a liquid, to recover a third stream rich in the protein-containing fermentation agent and a fourth stream comprising dissolved solids, suspended solids, or both in water.

2. The process according to claim 1, wherein the first separation stage comprises a mechanical separation stage.

3. The process according to claim 2, wherein the mechanical separation stage includes a decanting stage.

4. The process according to claim 1, wherein the first separation stage includes a centrifugal separation stage.

5. The process according to claim 1, wherein the second separation stage comprises a mechanical separation stage.

6. The process according to claim 5, wherein the mechanical separation stage of the second separation stage includes a centrifugal separation stage.

7. The process according to claim 6, wherein the centrifugal separation stage is carried out using a disk stack separator.

8. The process according to claim 7, wherein the third stream is subjected to a dewatering stage.

9. The process according to claim 8, wherein the dewatering stage comprises a mechanical dewatering stage.

10. The process according to claim 9, wherein the mechanical dewatering stage comprises subjecting the third stream to a filter press.

11. The process according to claim 8, further comprising drying the third stream, after the dewatering stage, to further reduce the moisture content.

12. The process according to claim 11, wherein the unfermented organic material is processed into a cake after separation from the co-product stream obtained from (i)-(iii) and wherein syrup is sprayed onto the cake, to produce distillers dark grains and solubles (DDGS).

13. The process according to claim 1, further comprising drying the third stream to reduce the moisture content.

14. The process according to claim 1, wherein the fourth stream is subjected to an evaporation stage to produce a syrup.

15. The process according to claim 1, wherein the organic material comprises a fermentable carbohydrate.

16. The process according to claim 1, wherein the organic material comprises a cereal grain, maize, wheat, sorghum or barley; potato; or beet molasses.

17. The process according to claim 1, wherein the protein-containing fermentation agent comprises fungal cells capable of fermenting the organic material to ethanol.

18. The process according to claim 1, wherein the protein-containing fermentation agent comprises a yeast.

19. The process according to claim 18, wherein the yeast is a yeast of the genus *Saccharomyces*.

20. The process according to claim 1, further comprising, after recovering the protein-containing fermentation agent, formulating the protein-containing fermentation agent as a feed additive in an animal feed composition.

21. The process according to claim 20, wherein the protein-containing fermentation agent comprises less than 2 wt % of the animal feed composition.

22. The process according to claim 1, comprising, after recovering the protein-containing fermentation agent, formulating the protein-containing fermentation agent as a protein source in a feed material in an animal feed composition.

23. The process according to claim 22, wherein the protein-containing fermentation agent comprises more than 2 wt % of the animal feed composition.

24. The process according to claim 22, wherein the protein-containing fermentation agent comprises more than 4 wt % of the animal feed composition.

25. The process according to claim 22, wherein the protein-containing fermentation agent comprises from 5 wt % to 40 wt % of the animal feed composition.

26. The process according to claim 22, further comprising combining the protein-containing fermentation agent with a carbohydrate source, and optionally an additional protein source, and optional additives, wherein the protein-containing fermentation agent comprises at least 2 wt % of the animal feed composition.

27. The process according to claim 1, wherein the unfermented organic material is processed into a cake after separation from the co-product stream obtained from (i)-(iii).

28. The process according to claim 27, wherein the co-product stream comprises water, protein-containing fermentation agent, suspended fibrous and proteinaceous non-fibrous solids, and dissolved solids comprising proteins.

29. The process according to claim 28, further comprising treating the co-product stream by separating the majority of the suspended fibrous solids from the rest of the co-product stream; and then separating the majority of the protein-containing fermentation agent from the water and dissolved solids.

30. The process of claim 1, wherein producing ethanol and a protein-containing fermentation agent according to (i)-(v) is carried out in an apparatus comprising:
  (i) a fermentation stage for fermenting an aqueous mixture comprising an organic material and the protein-containing fermentation agent capable of fermenting the organic material, to produce ethanol;
  (ii) a first separation stage for recovering the ethanol from the unfermented aqueous mixture;
  (iii) a second separation stage, downstream of the first separation stage for recovering unfermented organic material from the protein-containing fermentation agent and from an aqueous solution of dissolved solids in water; and
  (iv) a third separation stage, downstream of the second separation stage, for recovering the protein-containing fermentation agent from the aqueous solution.

* * * * *